United States Patent [19]

Sanders et al.

[11] Patent Number: 5,028,430

[45] Date of Patent: Jul. 2, 1991

[54] DELIVERY SYSTEMS FOR THE CONTROLLED ADMINISTRATION OF LHRH ANALOGS

[75] Inventors: Lynda M. Sanders, Palo Alto; Ramon A. Burns, Jr., San Jose, both of Calif.

[73] Assignee: Syntex (U.S.A.) Inc., Palo Alto, Calif.

[21] Appl. No.: 47,738

[22] Filed: May 8, 1987

[51] Int. Cl.$^5$ .................... A61F 2/00; A61K 31/74; A61K 31/00; A61K 31/02
[52] U.S. Cl. .................................... 424/423; 424/78; 514/15
[58] Field of Search ............... 514/15; 424/78, 423

[56] References Cited

U.S. PATENT DOCUMENTS

| | | | |
|---|---|---|---|
| 4,234,571 | 11/1980 | Nestor et al. | 514/800 |
| 4,391,797 | 7/1983 | Folkman et al. | 424/427 |
| 4,481,190 | 11/1984 | Nestor et al. | 530/328 |
| 4,581,169 | 4/1986 | Nestor et al. | 530/328 |
| 4,675,189 | 6/1987 | Kent et al. | 424/490 |
| 4,767,628 | 8/1988 | Hutchinson | 424/426 |

FOREIGN PATENT DOCUMENTS 021234 of 1981 European Pat. Off.
219076 of 1987 European Pat. Off.
246653 of 1987 European Pat. Off.

OTHER PUBLICATIONS

Langer et al., *Nature*, 263, 797 (1976).
Rhine et al., *J. Pharm. Sci.*, 69(3), 265 (1980).
Langer, et al., *J. Membrane Sci.*, 7, 333 (1980).
Brown et al., *J. Pharm. Sci.*, 72(10), 1181 (1983).
Bawa et al., *J. Controlled Rel.*, 1, 259 (1985).
Hsieh et al., *Pharmaceutical Technology*, Jun. 1985, pp. 39-48.
*Endocrine Rev.*, 7(1), 115 (1986).
Lotz et al., *J. Pharm. Pharmacol.*, 31, 649 (1979).
Rhine et al., "A New Approach to Achieve Zero—Order Release Kinetics From Diffusion—Controlled Polymer Matrix Systems" in *Controlled Release of Reactive Materials*, R. Baker, Ed., Academic Press, 1980.

*Primary Examiner*—Nathan M. Nutter
*Attorney, Agent, or Firm*—Tom M. Moran; Lester E. Johnson

[57] ABSTRACT

An implantable polymeric delivery system for the controlled and continuous administration of an LHRH agonist which comprises a silicone elastomer matrix in which is dispersed about 30 to about 42 weight percent of water-soluble particulate phase containing an LHRH analog or a pharmaceutically acceptable salt thereof.

30 Claims, 3 Drawing Sheets

Days After Implantation
41% [D-Nal (2), AzaGly] LHRH System

Days After Implantation
44% [D-Nal (2), AzaGly] LHRH System

DELIVERY SYSTEMS FOR THE CONTROLLED ADMINISTRATION OF LHRH ANALOGS

BACKGROUND OF THE INVENTION

This invention concerns a polymeric delivery system for the controlled and continuous administration of therapeutically effective amounts of LHRH analogs. More specifically, the invention relates to implantable silicone elastomer matrix systems which provide substantially constant and prolonged administration of therapeutically effective amounts of a luteinizing hormone-releasing hormone (LHRH) analog.

Continuous chronic administration of LHRH agonist and antagonist analogs has been found to block the secretion of gonadotropins in both male and female animals, thereby suppressing the production of gonadal steroids and gametes. As a result, such LHRH analogs have been indicated for controlling fertility, suppressing sexual behaviour in animals, causing regression of endometriotic lesions and prostatic cancers, and in the treatment of precocious puberty.

Conventional administration of LHRH analogs includes subcutaneous and intramuscular injections, and less commonly intranasal administration. Oral administration is impossible because the drugs are inactivated in the gastrointestinal tract. However, because LHRH analogs have short therapeutic half-lives ranging from several seconds to a few hours, frequent injections are necessary to achieve therapeusis, rendering chronic administration difficult and costly. A more useful approach is the implantation or other in situ application of long acting controlled release systems. In this way, active LHRH analog can be continuously delivered at therapeutic rates for prolonged periods without the necessity of daily or more frequent injections.

Diffusional matrix systems as devices for continuous drug administration in situ have significant commercial advantages in their ease and cost of manufacture when compared to other implantable drug delivery systems such as membrane controlled reservoir devices. Additionally, matrix type systems are one of the only means of achieving continuous controlled administration of macromolecular polypeptides, which do not diffuse readily across most polymeric membranes.

Langer et al. have demonstrated that macromolecules such as large polypeptides can be continuously released from ethylene vinyl acetate copolymer (EVA) matrices via diffusion through pores which are created in the matrix as the water-soluble particles of polypeptide are dissolved by incoming fluids. (See U.S. Pat. No. 4,391,797; Nature, Vol. 263, 797–799 (1976); Journal or Pharmaceutical Sciences, Vol. 69, No. 3, 265–270 (1980); Journal of Membrane Science, Vol. 7, 333–350 (1980); Journal of Pharmaceutical Sciences, Vol. 72, No. 10, 1181–1185 (1983); and Journal of Controlled Release, Vol. 1, 259–267 (1985)). However, the release rate of macromolecules from these systems has been shown to decrease with time, following (time)$^{-\frac{1}{2}}$ kinetics. Methods which have been implemented to achieve more nearly zero-order release with these systems include application of a thin membrane coating on all surfaces, covering all but a single surface with an impermeable material, and constructing the device so that only the surface from which release takes place is an inwardly releasing hemisphere (See, for example, "A New Approach to Achieve Zero—Order Release Kinetics From Diffusion—Controlled Polymer Matrix Systems" by Rhine et al. in *Controlled Release of Bioactive Materials*, R. Baker, Ed., Acacemic Press 1980).

Silicone elastomers have been used in both membrane controlled and matrix-type drug delivery systems for controlled administration of small, relatively water-insoluble molecules such as norgestrel, norethindrone, megestrol acetate and estradiol. The advantages of the silicone elastomers for parenteral in situ drug delivery include their long term proven biocompatibility, and their ease and low cost of fabrication. Curing can take place at room temperature, and organic solvents are not required. A perceived disadvantage however, has been their low permeability to water-soluble and large molecules.

Recently, Hsieh et al. described silicone elastomer matrices which released bovine serum albumin and other macromolecular polypeptides at a nearly constant rate in vitro for more than 100 days. (See Pharmaceutical Technology, June 1985, 39–48). However, to achieve a constant rate of release, these systems were encapsulated in an impermeable plastic (polyethylene or silicone rubber) tube which was coated at one end with an impermeable material, thus permitting release of drug from only the single circular surface at the open end of the tube, rather than from all surfaces of the matrix.

The formulation of LHRH analogs in matrix systems for long term drug delivery is particularly challenging because of their extremely high water-solubilities and potencies. Yet because of their high potencies, and their mechanism of action on the delicately balanced endocrine system, it is highly desirable that the rate of release achieved by such a system be constant as well as controlled. Implantable systems capable of controlled release of an LHRH analog for one month have been developed using a biodegradeable poly(lactide-co-glycolide) matrix in the form of microcapsules and larger implants. (See U.S. patent application Ser. No. 699,715 filed Feb. 8, 1985 and now U.S. Pat. No. 4,675,797 and EP Application No. 82300416. These systems operate by a combination of erosion and diffusion. However, they generally require the use of an organic solvent in fabrication. Additionally, they cannot be readily removed from the animal except during the very early period following implantation.

Thus, there is a need for a biocompatible delivery system capable of delivering therapeutic levels of LHRH analogs at constant rates for prolonged periods of time. Such a system should be a readily manufacturable monolithic device, without the additional requirements of impermeable coatings, membranes, microencapsulation and/or specialized device geometry.

SUMMARY OF THE INVENTION

Accordingly, it is an object of this invention to provide a monolithic silicone elastomer matrix delivery system for parenteral in situ administration of an LHRH analog at a constant and controlled rate to an animal in need of such treatment. The invention resides in the use of silicone elastomer as the matrix material, and in a window of effective loading levels for the water-soluble LHRH analog phase.

Surprisingly, it has now been found that the incorporation of about 30 to about 42 weight percent of a water-soluble, LHRH containing, particulate phase in a silicone elastomer matrix provides LHRH analog administration at essentially constant and therapeutically effective rates for prolonged periods of time. It has been found that this loading range of water-soluble solids is critical to obtaining constant long term LHRH analog delivery from a silicone elastomer matrix. The dependence of the in vivo LHRH analog release profile on loading level is so profound that a mere three percent increase in loading level above about 41 weight percent causes loss of the zero-order release profile and failure to maintain therapeutic levels of LHRH analog. Loading levels of water-soluble solids below about 30 weight percent do not provide sufficient particle contact for the development of pores within the matrix from which LHRH diffusional release can occur.

The invention is a polymeric delivery system for the controlled and sustained administration of an LHRH analog to an animal in need of such treatment, the system being sized and shaped for placement in the in situ environment of use and comprising a silicone elastomer matrix in which is dispersed about 30 to about 42 weight percent of a water-soluble particulate phase containing an LHRH analog or pharmaceutically acceptable salt thereof, wherein the delivery system provides essentially zero-order in vivo delivery of the LHRH analog at a therapeutically effective rate.

Another aspect of this invention resides in a method of administering an LHRH analog at an essentially constant therapeutically effective rate to an animal, which method comprises placing an appropriately sized and shaped delivery system of the above description in a body site which is capable of making available its intracellular and/or extracellular fluid for transfer into the system. Animals for which the systems of this invention may be particularly useful include dogs, cats, bovine animals, pigs, horses and humans.

Yet another aspect of this invention is a method of controlling fertility in animals which comprises placing an appropriately sized and shaped delivery system in a body site which is capable of making available its intracellular and/or extracellular fluid for transfer into the system, wherein the system provides essentially zero-order in vivo delivery of an LHRH analog at an effective rate, and comprises a silicone elastomer matrix in which is dispersed about 30 to about 42 weight percent of a water-soluble particulate phase containing an LHRH analog. Animals for which the systems of this invention may be particularly effective in controlling fertility include dogs, cats, bovine animals, horses and pigs, fish, zoo animals, birds and humans.

The systems of this invention provide all of the advantages of silicone elastomer matrices without the expected disadvantage of poor release kinetics or the requirement of specialized surface shapes and coatings; they are readily manufactured without organic solvents, are cured at room temperature, are cast, molded or otherwise readily shaped into simple shapes, do not require the application of rate controlling coatings or impermeable surfaces, are not encapsulated, and provide essentially zero-order release of LHRH analog for a period of at least six months. Other aspects and advantages of the invention will become apparent from the following more detailed description.

DETAILED DESCRIPTION AND PREFERRED EMBODIMENTS OF THE INVENTION

Figure 1:
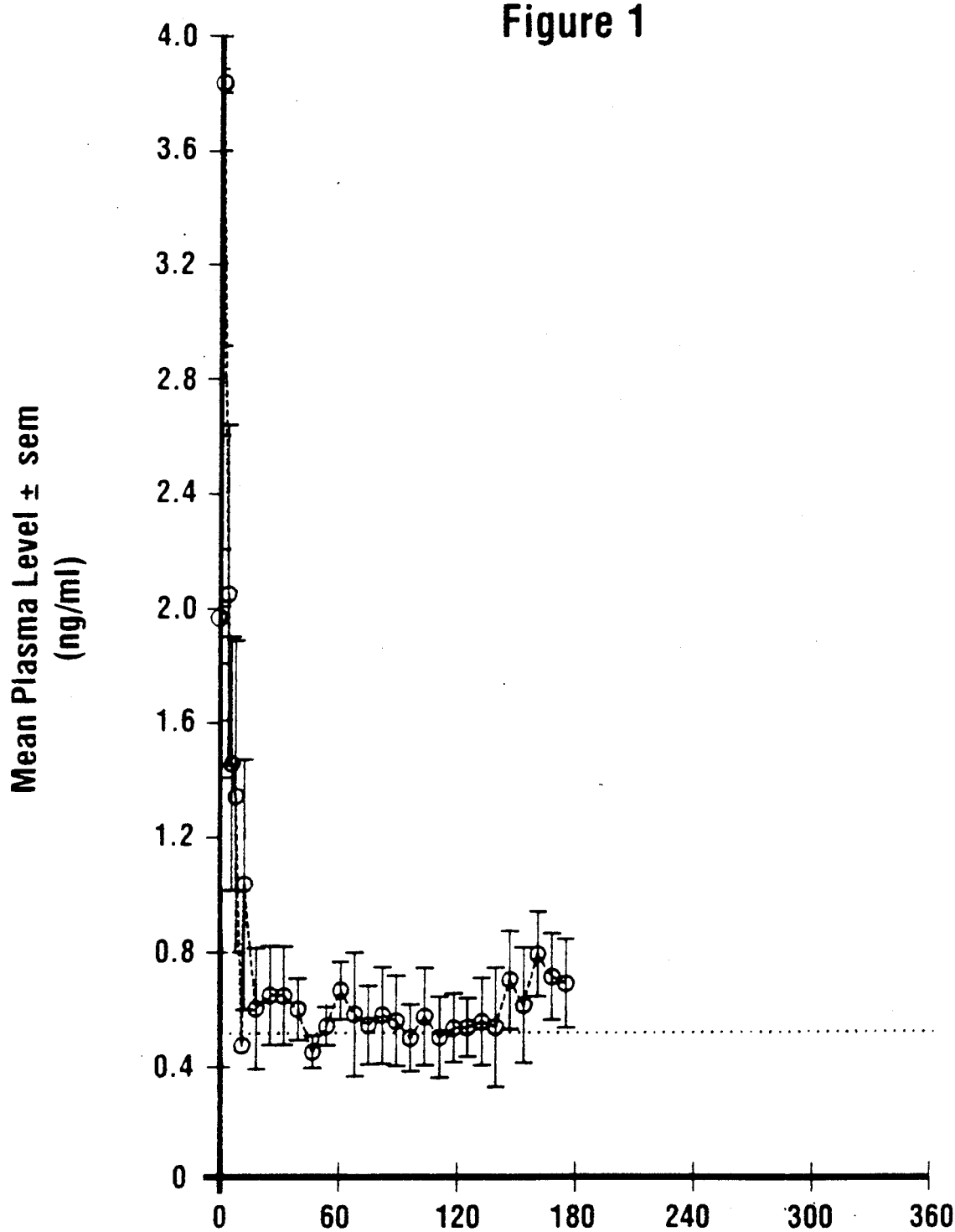
FIG. 1 is a graphical display of the results obtained from the experiment described in Example 2 and shows the plasma level of an LHRH analog achieved during subcutaneous implantation in dogs of a delivery system of this invention containing 39 weight percent LHRH analog.

The LHRH analog delivery systems of this invention provide several important advantages over previously known delivery systems. The most important advantage, as discussed above, is the provision of a matrix system which operates by diffusion and is capable of controlled and prolonged administration of the LHRH analog at a constant rate. Another important advantage of the claimed delivery systems is their ability to provide a range of useful release rates suitable for a variety of LHRH analogs, different animals and/or the requirements of different treatment regimens.

The system releases the LHRH analog when placed in situ at a body site which can make available its intracellular and/or extracellular fluid for transfer into the matrix. The fluid surrounding the system enters the polymer matrix as it dissolves exposed particles of water-soluble solids, thus creating channels or pores in the matrix as more and more water-soluble solids are dissolved. The LHRH analog, itself dissolved, diffuses from the matrix through the biological fluids in the pores of the matrix.

The term "matrix" as used herein denotes a solid phase carrier within which is dispersed a water-soluble particulate phase containing particles of LHRH analog and other optional water-soluble excipients. The carrier can be in any desired size and shape which is suitable for the intended use and in situ environment. Examples of readily manufacturable useful shapes include slabs, cylinders, spheres and the like.

The term "water-soluble particulate phase" denotes particles of water-soluble solids which are dispersed in the matrix. Thus the phrase refers to and includes the LHRH analog of choice and any optional pharmaceutically acceptable excipients which may be incorporated in the matrix and are at least very water-soluble. The water-soluble solids are in the form of particles which have diameters in the range of about 0.1 to about 500 microns. Water-soluble pharmaceutically acceptable materials which are liquids in a solitary state but are capable of being absorbed into and becoming part of the water-soluble particulate phase may be included in the phase at levels which do not cause the phase to lose its particulate conformation and/or change from the solid state to a semi-solid or liquid state.

The term "very slightly soluble" as used herein, refers to a solubility of at least about 0.1 mg/ml.

The terms "in situ" and "body site" are used herein to denote the placement and operation of a delivery system in an animal at a particular site. For successful operation of the delivery systems of this invention, such sites should be capable of making available their intracellular and or extracellular fluids for transfer into the system. Suitable in situ body sites include, but are not limited to, the subcutaneous space, the cul de sac of the eye, the eyeball, vagina, uterus, rectum and the like.

The term "animal" as used herein refers to all animals in which LHRH analogs display useful pharmacologic effects. These include, but are not limited to mammals including humans, horses, bovine, pigs, primates and the like, birds, and fish. The systems of this invention have particular utility in humans, in pets such as dogs and cats, in animal husbandry species such as cattle, pigs, horses, chicken, turkey and fish, and in captive zoo animals such as lions, tigers, elephants, primates and the like.

The term "therapeutically effective" as used herein refers to a rate and means of drug administration which provides LHRH analog plasma levels which are effective to achieve the desired pharamcologic result. For example, if the plasma level required to achieve and maintain estrus suppression in large female dogs with a particular LHRH analog is approximately 0.3 ng/ml, a therapeutically effective delivery rate would be one which provides average plasma levels of that drug at or above 0.3 ng/ml.

The terms "essentially zero-order" and "essentially zero-order in vivo delivery" as used herein mean that delivery systems within the definition of this invention provide in vivo delivery of an LHRH analog at a substantially constant average rate following an initial burst period (which generally lasts less than one month) throughout the remainder of the release period for which the system is intended to provide efficacious plasma levels. Preferably, the rate of release will decline less than about 20 percent during the last 90 percent of the intended duration of release. Because the LHRH analogs have very short biological half-lives of a few hours or less, the rate, duration and profile of in vivo delivery can be closely monitored by assays of plasma samples which are taken at regular intervals following implantation or other in situ application of a particular system.

For convenience in describing and naming the various nona- and decapeptides within the class of LHRH angonist and antagonist analogs, the conventional abbreviations for individual amino acids are used which are recommended by the IUPAC-IUB Commission on Biochemical Nomenclature, Biochemistry, 11, 1726 (1972) and as generally accepted in the peptide art. As used herein, the abbreviations represent L-amino acids unless otherwise noted, and all peptide sequences are written according to the generally accepted convention whereby the N-terminal acid is shown on the left, and the C-terminal acid is shown on the right.

The preferred LHRH analog for use in this invention is L-pyroglutamyl-L-histidyl-L-tryptophyl-L-seryl-L-tyrosyl-D-3-(2-naphthyl)alanyl-L-leucyl-L-arginyl-L-prolyl-azaglycinamide acetate. For convenience, this compound is alternatively referred to herein as (pyro)-Glu-His-Trp-Ser-Tyr-D-3-(2-naphthyl)alanyl-leu-Arg-Pro-azaglycine amide acetate, or by the further abbreviated form, [D—Nal(2)$^6$, Azagly$^{10}$]LHRH.

The delivery systems of the invention comprise a matrix of water-insoluble silicone elastomer polymer which is itself substantially impermeable to macromolecules, in which is dispersed a water-soluble particulate phase containing an LHRH analog. Surprisingly, it has been found that when the water-soluble particulate phase represents about 30 to about 42 weight percent of the matrix, the LHRH analog diffuses from the matrix in a manner which provides essentially constant (zero-order), and therapeutically effective plasma levels over periods of at least six, and preferably twelve months.

Figure 2:
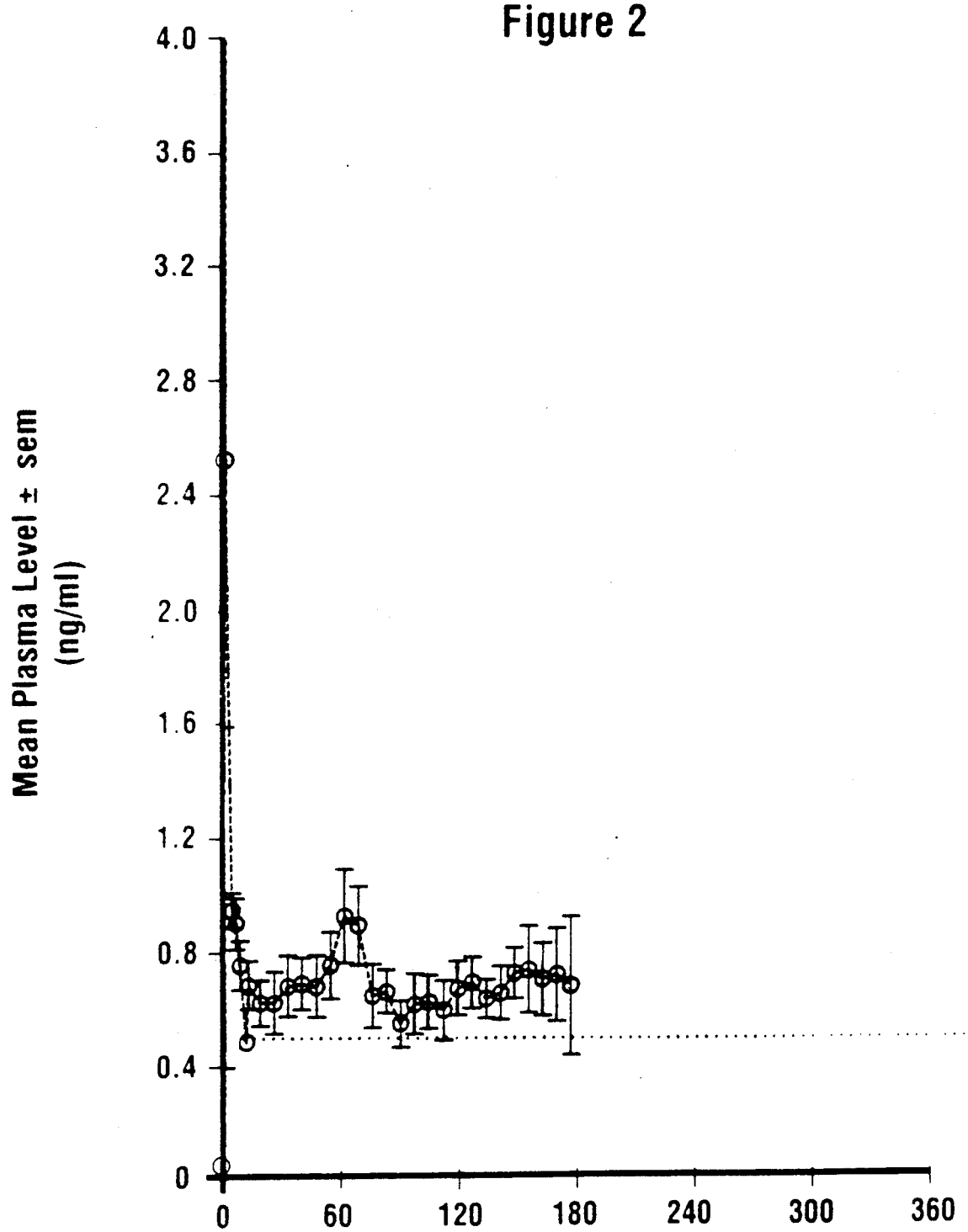
FIG. 2 is a graphical display of the results obtained from the experiment described in Example 2 and shows the plasma level of an LHRH analog achieved during subcutaneous implantation in dogs of a delivery system of this invention containing 41 weight percent LHRH analog.
Figure 3:
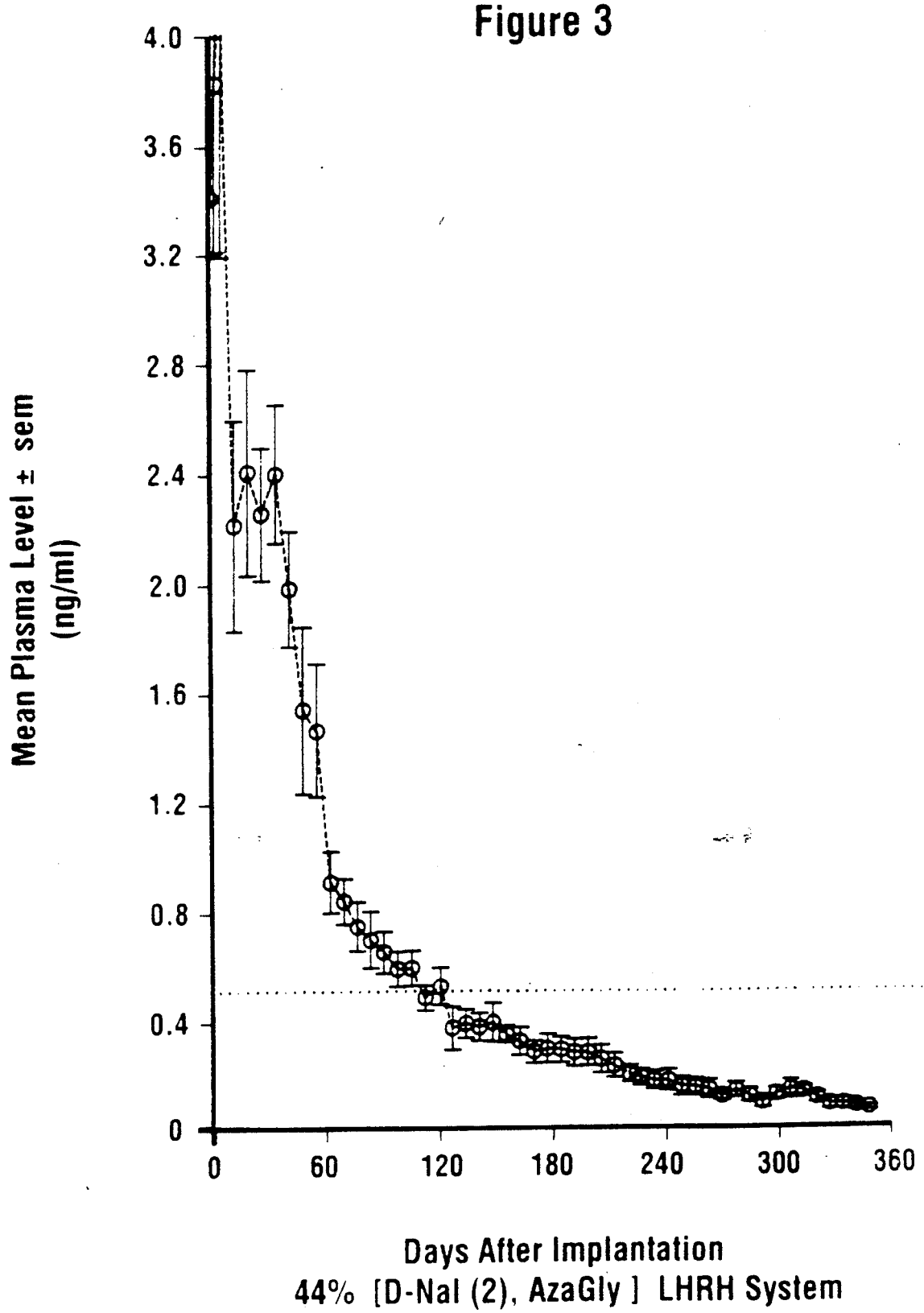
FIG. 3 is a graphical display of the results obtained from the experiment described in Example 2 and shows the plasma level of an LHRH analog achieved during subcutaneous implantation in dogs of a silicone elastomer matrix system containing 44 weight percent LHRH analog.

As shown in FIGS. 1 and 2, delivery systems manufactured according to the invention containing 39 and 41 weight percent LHRH analog, respectively, demonstrate in vivo release profiles which are essentially zero-order from about day 19 through the sixth month of subcutaneous implantation in the dog. In contrast, as shown in FIG. 3, an otherwise identical delivery system containing 44 weight percent LHRH analog demonstrated a rapidly declining release profile, with drug delivery falling below therapeutic levels between 100 and 160 days after implantation.

LHRH analogs comprise a large group of structurally related nona- and decapeptide analogs of naturally occuring LHRH. They are all water-soluble, polar molecules having molecular weights of about 1100–1300. The naturally occuring LHRH peptide is produced in the hypothalmic region of the brain and controls the reproductive cycle of animals by acting on the anterior pituitary gland to effect release of luteinizing hormone (LH) and follicular stimulating hormone (FSH) which in turn act on the gonads to stimulate the synthesis of steroid hormones and to stimulate gamete maturation. The pulsatile release of LHRH thereby controls the reproductive cycle in animals. Additionally, LHRH has effects in the placenta, in releasing HCG, and directly on the gonads.

Thus, the delivery systems of this invention may be designed and used for a wide variety of different therapeutic applications in humans and other animals. These include, but are not limited to contraception, fertility control, suppression or interruption of heat, treatment of ovarian cysts, prostatic hyperplasia and tumors, and termination of pregancy. The knowledge of specific utilities of LHRH analogs in various species is rapidly growing; the purpose of this invention is to provide a practical means of delivering the LHRH analog at a controlled rate, without being limited to any particular therapeutic application. However, specific utilities for which the invention may be particularly advantageous include the control of fertility in dogs, cats, cattle, horses, zoo animals and the like, the control of egg production in birds such as chickens and turkeys, and the control of breeding by inducement of spawning in fish raised by aquaculture. For a summary of potential therapeutic utilities of LHRH analogs, see Endocrine Review, Vol. 7, No. 1, 115–124 (1986).

Agonist analogues of LHRH are useful for the control of fertility by two mechanisms of action. Low doses of LHRH analogues can stimulate ovulation and are useful in the treatment of hypothalmic and ovulatory infertility. Additionally they can be used for hypogonadal conditions and impotence, and to stimulate spermatogenesis and androgen production in the male.

Paradoxically, larger doses of highly potent and long-lasting analogues of LHRH have an opposite effect, blocking ovulation in the female and suppressing spermatogenesis in the male. Related to these effects is a suppression of normal circulating levels of sexual steroids of gonadal origin, including reduction in accessory organ weight in the male and female. In domestic animals this paradoxical effect promotes weight gain in a feed-lot situation, stimulates abortion in pregnant animals and in general, acts as a chemical sterilant. A full list of the paradoxical high dose effects is set out in U.S.

Pat. No. 4,234,571, the entirety of which is incorporated by reference herein.

There is also the group of LHRH analogues termed antagonists. These polypeptides have the paradoxical effect shown by LHRH agonists but at low dose levels relative to naturally occuring LHRH. Such compounds are to be included within the scope of this invention. Particularly potent LHRH antagonists are described in U.S. Pat. Nos. 4,481,190 and 4,581,169, and in U.S. patent application Ser. No. 495,226 filed May 20, 1983 and now U.S. Pat. No. 4,667,019, each of which is incorporated by reference herein.

The natural LHRH peptide is a decapeptide comprised of naturally occuring amino acids (which have the L-configuration except for the achiral amino acid glycine). Its sequence is as follows: (pyro)Glu-His-Trp-Ser-Tyr-Gly-Leu-Arg-Pro-Gly-$NH_2$. Many analogues of this natural material have been studied. The beneficial effectiveness of these analogues has been varied. The most significant modification where agonists are concerned is obtained by changing the 6-position residue from Gly to a D-amino acid, for example, D-Ala, D-Leu, D-Phe or D-Trp. Antagonist activity can be best realized by substituting the naturally occuring 2-position His amino acid residue with with a D-amino acid residue. These analogues show increased activity relative to LHRH.

In addition to modifications at position 6, increased agonist activity may be obtained by the following modifications: modifying position 10 to afford a nonapeptide as an alkyl-, cycloalkyl- or fluoroalkyl-amine, or by replacing Gly-$NH_2$ by an α-azaglycine amide; substituting N-methyl-leucine for leucine in position 7; replacing tryptophan in position 3 by 3-(1-naphthyl)-L-alanine; substituting the position 5 tyrosine residue with phenylalanine or 3-(1-pentafluorophenyl)-L-alanine; and the substitution at position 6 of unnatural D-amino acid residues containing two or more carbocyclic (or perhydroaryl) rings or a phenyl (or cyclohexyl) ring which is highly alkyl substituted. These specific compounds represent some of the more useful fertility affecting LHRH type polypeptides which have been developed to date. This is not intended to be an exhaustive or exclusive list of all LHRH active polypeptides which have been made or which can or may be made. They are simply set out to illustrate the type of compounds which are the subject of this invention. Any or all of them can be interchangeably substituted into the compositions of this invention.

The LHRH compounds of particular interest herein are agonists from the last mentioned group wherein the 6-position of the naturally occuring LHRH material is replaced with a specific non-natural D-amino residue containing lipophilic carbocyclic residues, particularly residues containing two or more highly alkyl substituted carbocyclic aryl (or perhydroaryl) rings or a phenyl (or cyclohexyl) ring. These particular polypeptides are the subject of U.S. Pat. No. 4,234,571 and are prepared in accordance with the procedures set forth therein. That patent is incorporated in full herein by reference and made a part of this application. Reference is made to that application for a full description of the synthetic nonapeptides and decapeptides of most interest herein. A full description of the formulas, nomenclature and synthetic methods for preparing these compounds are found therein. The compounds set out therein comprise the preferred embodiment of synthetic LHRH analogues for incorporation into the delivery systemts of this invention.

More specifically the LHRH polypeptides of particular interest in this invention are the nonapeptides and decapeptides of the formula:

(pyro)Glu-His-V-Ser-W-X-Y-Arg-Pro-Z   (1)

and the pharmaceutically acceptable salts thereof wherein:

V is tryptophyl, phenylalanyl or 3-(1-naphthyl)-L-alanyl;

W is tyrosyl, phenylalanyl or 3-(1-pentafluorophenyl)-L-alanyl;

X is a D-amino acid residue

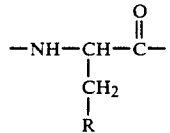

wherein R is (a) a carbocyclic aryl-containing radical selected from the group consisting of naphthyl, anthryl, fluorenyl, phenanthryl, biphenyl, benzhydryl and phenyl substituted with three or more straight chain lower alkyl groups; or (b) a saturated carbocyclic radical selected from the group consisting of cyclohexyl substituted with three or more straight chain lower alkyl groups, perhydronaphthyl, perhydrobiphenylyl, perhydro-2,2-diphenylmethyl and adamantyl;

Y is leucyl, Isoluecyl, nor-leucyl or N-methl-leucyl;

Z is glycinamide or —NH—$R_1$, wherein $R_1$ is lower alkyl, cycloalkyl, fluoro lower alkyl or

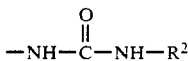

$R_2$ is hydrogen or lower alkyl.

The most preferred LHRH-active synthetic nona- and decapeptides of this invention are those compounds of formula 1 wherein X is 3-(2-naphthyl)-D-alanyl or 3-(2,4,6-trimethylphenyl)-D-alanyl; Z is azaglycine amide or glycinamide; V is tryptophyl or phenylalanyl; W is tyrosyl and Y is leucyl or N-methyl-leucyl.

The most preferred LHRH analogs for use in the delivery systems of this invention are:

(pyro)Glu-His-Trp-Ser-Tyr-3-(2-naphthyl)-D-alanyl-Leu-Arg-Pro-azaglycine amide;

(pyro)Glu-His-Trp-Ser-Tyr-3-(2-naphthyl)-D-alanyl-leu-Arg-Pro-Gly-$NH_2$;

(pyro)Glu-His-Trp-Ser-Tyr-3-(2-naphthyl)-D-alanyl-n-methyl-Leu-Arg-Pro-Gly-$NH_2$;

(pyro)Glu-His-Phe-Ser-Tyr-3-(2-naphthyl)-D-alanyl-Leu-Arg-Pro-Gly-$NH_2$;

(pyro)Glu-His-Trp-Ser-Tyr-3-(2,4,6-trimethylphenyl)-D-alanyl-Leu-Arg-Pro-Gly-$NH_2$;

(pyro)Glu-His-Trp-Ser-Tyr-3-(2-naphtyl)-D-alanyl-Leu-Arg-Pro-NHEt;

(pyro)Glu-His-Trp-Ser-Tyr-3-(2-naphtyl)-D-alanyl-N-methyl-Leu-Arg-Pro-NHEt;

and their pharmaceutically acceptable salts.

Especially preferred is (pyro)Glu-His-Trp-Ser-Tyr-D-3-(2-naphthyl) alanyl-leu-Arg-Pro-azaglycine amide acetate.

Depending on the particular choice of LHRH analog and the intended application, the LHRH analog active agent can make up the entire water-soluble phase of the delivery system matrix, or can be combined with other pharmaceutically acceptable water-soluble excipients in amounts which total 30–42 weight percent water-soluble particulate solids. The amount of LHRH analog which is incorporated in the water-soluble phase will depend upon the specific rate of release which is required and may be as little as 1 weight percent of the matrix. Additional amounts of optional water-soluble particulate excipients will then be incorporated which bring the total loading level of water-soluble particulate solids in the matrix to within the range of about 30 to about 42 weight percent. Where the LHRH analog is a compound of formula 1 as described herein, it will preferably comprise at least 30 weight percent, and more preferably 39–42 weight percent, of the matrix. At present, the most preferred delivery systems of the invention contain 39–42 weight percent LHRH analog without additional optional excipients.

If excipients are incorporated in the water-soluble phase, they must be at least very slightly water-soluble. Water-soluble excipients which may be useful in the practice of this invention include, but are not limited to other active agents, proteins or other polypeptides, stabilizers, buffers, salts, surfactants, stabilizers and fillers. Specific examples of optional water-soluble excipients include but are not limited to human serum albumin, gelatin, dextrose, sucrose, maltose, mannose, glucose, fructose, and lactose. Normally liquid water-miscible excipients which can be included in minor amounts include glycerol, propylene glycol, polyethylene glycol of various molecular weights, sorbitol and the like. Virtually any material which is pharmaceutically acceptable for parenteral administration and which is at least very slightly water soluble can be incorporated in the water-soluble phase. Such materials are well known in the pharmaceutical formulation art; standard pharmceutical texts such as *Remington's Practice of Pharmacy*, Sixteenth Edition (1980) contain descriptions of long lists of suitable excipients which are water-soluble.

The silicone elastomers suitable for use in this invention are a family of polymers and copolymers having backbone structures made up of alternating silicone and oxygen atoms. Typically, the silicone atoms have one or more organic side groups attached to them, generally phenyl, methyl and/or vinyl units. The most widely used silicone elastomers in the medical field are polydimethylsiloxane polymers with a general structural formula of

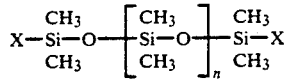

The number n of dimethylsiloxy units indicates the average length of the polymer chain in a particular elastomer, and determines the viscosity of that elastomer.

The silicone elastomers are generally prepared from silicone polymer chains bearing reactive diol terminal X groups, and are cured by either room temperature vulcanization or heat vulcanization. Room temperature vulcanization is the preferred method in this invention. However, heat vulcanization can be used if additional cross-linking of the polymer chains is desired. The silicone elastomers often contain non-water-soluble fillers such as silica or diatomaceous earths, which are added to strengthen the polymer. Non-water-soluble materials may be incorporated in the silicone elastomer within the practice of this invention to the extent that the resulting delivery systems provide essentially zero-order in vivo LHRH analog administration.

Silicone elastomers of the type represented by Silastic ® 382 medical grade elastomer, available from Dow Corning Corporation, Midland, Mich., are the most preferred medical grade room temperature vulcanizing elastomers for fabricating the invention systems. The polymer base of Silastic ® 382 medical grade elastomer is composed of chains of polydimethylsiloxane of the structure shown above (in which both X's are OH groups) and a crosslinking agent such as propyl orthosilicate. When an appropriate catalyst, such as stannous octoate, is added to the polymer base, the hydroxy terminal groups on the polymer chains react with the alkyl groups of the cross-linking agent to form the rubbery vulcanized elastomer in its final form. The skilled pharmaceutical chemist will appreciate that a variety of structurally similar biocompatible silicone elastomers are commercially available which can also be used to form the delivery systems of this invention. These include, but are not limited to one and two component cure-systems of silicone polymers and copolymers such as the Silastic ® medical grade ETR elastomers and the MDX-4-4210 clean grade elastomer available from Dow Corning. Suitable catalysts are available for each of the commercially available silicone elastomers, and include stannous octoate and platinum metal-based catalysts.

In accordance with the present invention, an LHRH analog of choice is delivered at a constant and controlled rate over a prolonged period of time, preferably ranging from six months to a year or more. Because these nona- and decapeptides do not diffuse through the chains of the silicone polymer itself, it is believed that drug release from these delivery systems occurs via diffusion through pores developed in the matrix from previously dissolved particles of drug or other components of the water-soluble phase.

Thus, the LHRH analog and optional water-soluble components should be in the form of solid particles ranging in size from about 1 to about 500 microns. Preferably, these particles will be agglomerates of smaller primary particles having diameters in the range of less than 0.1 micron to about 1 micron. In preparing the LHRH analog for incorporation in the matrix, it can be lyophilized, precipitated, ground, or otherwise prepared in particulate form.

A particularily preferred form of the LHRH analog results from precipitation of the analog from solution, followed by grinding to a fine powder, and subsequent humidification. For example, a solution of the LHRH analog in a solvent such as methanol, methanol/acetic acid mixtures, or preferably, acetic acid, is slowly added with stirring to anhydrous ether. The precipitated mixture is filtered, and the precipitate washed with additional anhydrous ether and dried in a vacuum oven under nitrogen for several days. The peptide is then ground to a fine powder, and subsequently humidified in a humidity chamber for several days. Further description of this method can be found in Example 1.A below.

In fabricating the delivery systems of this invention, the LHRH analog and any optional water-soluble components are mixed with the elastomer components prior to curing. While sufficient mixing should take place to achieve a substantially uniform dispersion, there is no particular type of mixing equipment which must be used. Typically, the LHRH analog, or a mixture of LHRH analog and optional water soluble excipients, is added to the polymer base and mixed thoroughly to achieve a substantially uniform dispersion of water-soluble components in the base. An appropriate catalyst is then added and further mixing is performed. At this point, the LHRH analog/silicone elastomer mixture can be cast, poured, molded or otherwise shaped to a desired form, and allowed to vulcanize, preferably at room temperature.

In determining the amounts of each component of the matrix, the actual amount of LHRH analog and any optional water-soluble excipients in the water-soluble particulate phase will be calculated as the percentage of water-soluble solids relative to the total weight of all components of the system, and should be in the range of about 30 to about 42 weight percent. In this regard, it should be noted that the LHRH analogs, and perhaps some excipients, may be partially hydrated—that is, they may contain small percentages of water. The 30 to 42 percent required loading level of water-soluble components includes the water of hydration present in any water-soluble component. Additionally, any amount of acetate or other salt which is present in association with the LHRH analog is included in calculation the loading level of water-soluble components. The amount of catalyst which is used to vulcanize the polymer base will vary according to the requirements of the particular system, generally in the range of about 1 to 40, preferably 20 to 40 µl catalyst/gram of base. The amount of catalyst required is readily determined by the formulating chemist based on reccomendations of the elastomer manufacturer and general knowledge in the polymer arts.

An advantage of the silicone elastomer matrix is the ease and versatility with which it can be fabricated into devices of varied sizes and shapes, thus permitting optimization of conformation of the delivery system for particular in situ environments. Prior to vulcanization, the elastomer/drug dispersion can be formed by molding, casting, pressing, extruding, drawing and other procedures conventionally used to fabricate silicone elastomers. Subsequent to vulcanization, the hardened matrix can be further shaped and sized by cutting or other sculpting means.

For example, a simple and preferred method of system fabrication entails molding the drug/elastomer dispersion in a slab conformation, followed by cutting the slab into rectangular or other shaped systems of the desired size with a sharp cutting tool. The presence of surfaces on the system which have been cut subsequent to vulcanization enhances total drug delivery (drug utilization) from the system. Accordingly, in preferred embodiments of the invention, at least about 5 percent, more preferably at least about 50 percent, and most preferably about 60 to 80 percent of the system surface will be cut subsequent to vulcanzation.

The delivery devices of this invention can be designed to deliver the biologically active LHRH analog at a controlled and constant rate over a prolonged period of time ranging from one month to more than one year, preferably for at least six months. Examples of systems which delivered therapeutically useful levels of (pyro)Glu-His-Trp-Ser-Tyr-D-3-(2-naphthyl) alanyl-leu-Arg-Pro-azaglycine amide acetate subcutaneously over a period of more than six months are described in Examples 1 and 2 and the resulting in vivo plasma profiles are shown in FIGS. 1 and 2.

The actual rate and duration of LHRH delivery can be varied within the practice of this invention and tailored to specific requirements by the choice of silicone elastomer, the size of the system, the proportion of cut surfaces on the system, and the proportion of drug in the water-soluble phase.

PREFERRED EMBODIMENTS

At the present time, the preferred LHRH analogs for use in this invention are the LHRH agonists of formula 1, as described hereinabove. Particularly preferred among these is (pyro)Glu-His-Trp-Ser-Tyr-3-(naphthyl)-D-alanyl-leu-Arg-Pro-azaglycine amide acetate.

The presently preferred delivery systems of the invention comprise a silicone elastomer matrix, more preferably a polydimethylsiloxane matrix, in which is dispersed about 35 to about 42, more preferably about 39 to about 42 weight percent of a water-soluble particulate phase containing an LHRH analog. Most preferably, the delivery systems will consist essentially of the polydimethylsiloxane matrix in which is dispersed about 39 to about 42 weight percent (pyro)Glu-His-Trp-Ser-Tyr-D-3-(2-naphthyl)alanyl-leu-Arg-Pro-azaglycine amide acetate. A particularly preferred delivery system consists essentially of a polydimethylsiloxane matrix in which is dispersed about 41 weight percent (pyro)Glu-His-Trp-Ser-Tyr-D-3-(2-naphthyl)alanyl-leu-Arg-Pro-azaglycine amide acetate.

In all embodiments, the LHRH analog is preferably in the form of agglomerates of primary particles, wherein the primary particles have diameters in the range of less than 0.1 to about 1 micron, and the agglomerates have diameters in the range of less than 1 to about 500 microns. More preferably, the water-soluble particulate phase as a whole will consist susbstantially of such agglomerates of agglomerates of primary particles.

Additionally, in fabricating the delivery systems of the invention, it is preferably to size and shape the individual delivery systems after vulcanization of the polymer by a cutting procedure such that at least 5 percent, preferably at least 50 percent, and more preferably about 60 to 80 percent of the system surface is cut.

The following Examples are provided to further illustrate the practice of this invention, and are not intended to in any way limit its scope.

EXAMPLE 1

Preparation of Systems Providing Zero-Order Delivery of an LHRH Analog

A. Silicone elastomer matrix delivery systems containing 39 and 41 weight percent LHRH analog were prepared according to the invention as follows:

A clarified solution of (pyro)Glu-His-Trp-Ser-Tyr-D-3-(2-naphthyl)alanyl-leu-Arg-Pro-azaglycine amide acetate in acetic acid (10 ml/g) was added in a slow stream to anhydrous diethyl ether (100–200 ml/g) with stirring. After filtering, the wet cake was washed with anhydrous ether, placed in a vacuum oven and dried under nitrogen for several days. The peptide was then ground to a fine powder with a spatula and subsequently humidified in a humidity chamber (relative humidity 85%) for several days.

Silastic ® 382 medical grade elastomer base, which had been stored under refrigeration, was warmed to room temperature and weighed onto a teflon coated surface. The elastomer base was then degassed for about 10 minutes under vacuum. The precipitated and ground (pyro)Glu-His-Trp-Ser-Tyr-D-3-(2-naphthyl)alanyl-leu-Arg-Pro-azaglycine amide acetate was weighed and added in the targeted amount to the silastic base. The elastomer base and LHRH analog were then mixed thoroughly with two stainless steel spatulas. Catalyst M (stannous octoate) was added from a syringe and further mixing was performed. Actual amounts of LHRH analog, Silastic ® 382 base and Catalyst M used to manufacture the 39 and 41 weight percent LHRH analog systems are given below:

| Ingredient | Systems Containing 39 percent LHRH analog | Systems Containing 41 percent LHRH analog |
| --- | --- | --- |
| Silastic ® 382 base | 0.7747 g | 1.2341 g |
| LHRH analog* | 0.5191 g | 0.8899 g |
| Catalyst M[1] | 0.0298 g | 0.0562 g |

*(pyro)Glu—His—Trp—Ser—Tyr—D-3-(2-naphthyl)alanyl-leu—Arg—Pro-azaglycine amide acetate
[1]stannous octoate The 39 and 41 percent loaded mixtures thus prepared were placed in rectangular slab shaped molds of dimensions 3 mm × 14 mm × 19 mm, and 3 mm × 15 mm × 16 mm, respectively, with care taken to avoid entrapment of air within the mixtures. Excess mixture was used to insure filling of the molds. The molds containing the drug/elastomer mixtures were then placed in a vacuum dessicator for a period of one to three days, during which vulcanization was completed. The resulting molded matrices were then sliced into rectangular slab shaped systems of dimensions 1 mm × 3 mm × approximately 14 mm to achieve individual units which, based on their weights, contained 20 mg of the hydrated acetate salt of (pyro)Glu-His-Trp-Ser-Tyr-D-3-(2-naphthyl)alanyl-leu-Arg-Pro-azaglycine amide. Each unit had approximately 70 percent of its surface cut, and approximately 30 percent of its surface remained as molded. The systems were sterilized by gamma irradiation at 1.25 MRad.

B. In a similar manner, but modifying the proportions of components, substituting other LHRH analogs and/or other silicon elastomers, and if desired, incorporating additional water-soluble particulate excipients, other delivery systems within the spirit of this invention may be readily manufactured.

EXAMPLE 2

Preparation of System Containing 44 Weight Percent LHRH Analog

Following the method described in Example 1.A, above, delivery systems were prepared from a drug/elastomer mixture of the following formulation:

| Ingredient | Systems Containing 44 percent LHRH analog |
| --- | --- |
| Silastic ® 382 base | 1.0230 g |
| LHRH analog* | 0.8369 g |
| Catalyst M[1] | 0.0362 g |

*(pyro)Glu—His—Trp—Ser—Tyr—D-3-(2-naphthyl)alanyl-leu—Arg—Pro-azaglycine amide acetate
[1]stannous octoate This drug/elastomer mixture was molded, cut into individual systems and sterilized as described in Example 1.A, above, giving individual delivery system units containing 44 weight percent LHRH analog as the water-soluble particulate phase.

EXAMPLE 3

Plasma Profile of LHRH Analog Achieved From Subcutaneous Implantation of Delivery Systems in Dogs Samples of the 39 and 41 weight percent LHRH analog systems prepared as described in Example 1.A, and the 44 weight percent systems prepared as described in Example 2, were subcutaneously implanted in adult male and female beagles, and the resulting plasma levels of LHRH analog monitored, as follows: Each implant contained a total dose of 20 mg (pyro)Glu-His-Trp-Ser-Tyr-D-3-(2-naphthyl)alanyl-leu-Arg-Pro-azaglycine amide acetate. Two male dogs and two bitches (Group 1) were each implanted with single 39 percent systems. Three male dogs and four bitches (Group 2) were each implanted with single 41 percent systems. Three male dogs and three female dogs (Group 3) were each implanted with single 44 percent systems. Plasma samples were collected at regular intervals from each dog and assayed for levels of (pyro)Glu-His-Trp-Ser-Tyr-3-(naphthyl)-D-alanyl-leu-Arg-Pro-azaglycine amide acetate by radioimmunoassay. The individual plasma levels obtained at each sampling period were averaged within each Group (1, 2 and 3).

The resulting average plasma level profiles of LHRH analog in dogs in each of Groups 1, 2 and 3 are shown in FIGS. 1, 2 and 3, respectively, in which the vertical bars indicate standard errors of the mean. FIG. 1 shows plasma (pyro)Glu-His-Trp-Ser-Tyr-3-(naphthyl)-D-alanyl-leu-Arg-Pro-azaglycine amide acetate levels from 39 percent loaded systems in male and female beagles over a period of 180 days after subcutaneous implantation; plasma drug levels are maintained at or slightly above about 0.5 ng/ml from about day 19. FIG. 2 shows plasma (pyro)Glu-His-Trp-Ser-Tyr-D-3-(2-naphthyl)alanyl-leu-Arg-Pro-azaglycine amide acetate levels from 41 percent loaded systems in male and female beagles over the same period after subcutaneous implantation; plasma drug levels are maintained at or slightly above about 0.6 ng/ml from about day 19. The plasma levels achieved with both the 39 and 41 percent loaded systems were substantially constant after day 19 following implantation and show no signs of decline. Suppression of estrus in the females, and of testosterone production in the males, was achieved and maintained through the duration of the study in all animals. The systems which are implanted in these dogs contain adequate LHRH analog for continued constant delivery for at least one year.

FIG. 3 shows plasma (pyro)Glu-His-Trp-Ser-Tyr-D-3-(2-naphthyl)alanyl-leu-Arg-Pro-azaglycine amide acetate levels from 44 percent loaded systems in male and female beagles over the same period after subcutaneous implantation; in contrast to the essentially constant plasma profiles shown in FIGS. 1 and 2 for the 39 and 41 percent systems, the 45 percent implants released a large fraction of the total drug contained in the system in the first sixty days after implantation. At that point, insufficient drug remained in the systems, and plasma drug levels steadily decayed in a (time)$^{-\frac{1}{2}}$ dependent manner. The average plasma level fell below the targeted efficacious 0.5 ng/ml level at approximately 110 days. While estrus and testosterone production were initially suppressed, estrus recurred and testosterone levels returned to normal in several animals during the latter months of the study.

We claim:

1. A polymeric delivery system for the controlled and sustained administration of an LHRH analog to an animal in need of such treatment, the system being sized and shaped for placement in the in situ environment of use and comprising a silicone elastomer matrix in which is dispersed about 30 to about 42 weight percent of a water-soluble particulate phase containing an LHRH analog or pharmaceutically acceptable salt thereof, wherein the delivery system provides essentially zero-order in vivo delivery of the LHRH analog at a therapeutically effective rate.

2. A system of claim 1 in which the LHRH analog is a particulate comprised substantially of agglomerates of primary particles, wherein the primary particles have diameters in the range of less than 0.1 micron to about 1 micron, and the agglomerates have diameters in the range of less than 1 to about 500 microns.

3. A system of claim 1 in which at least 5 percent of the system surface is cut and the remainder is uncut.

4. A system of claim 3 in which at least 50 percent of the system surface is cut and the remainder is uncut.

5. A system of claim 1 in which the water-soluble particulate phase comprises about 35 to about 42 weight percent of the matrix.

6. A system of claim 5 in which the water-soluble particulate phase comprises about 39 to about 42 weight percent of the matrix.

7. A system of claim 6 in which the water-soluble particulate phase consists essentially of an LHRH analog or a pharmaceutically acceptable salt thereof.

8. A system of claim 1 in which the LHRH analog is a compound of the formula:

(pryo)Glu-His-V-Ser-W-X-Y-Arg-Pro-Z      (1)

or a pharmaceutically acceptable salt thereof wherein:

V is tryptophyl, phenylalanyl or 3-(1-naphthyl)-L-alanyl;

W is tyrosyl, phenylalanyl or 3-(1-pentafluorophenyl)-L-alanyl;

X is a D-amino acid residue

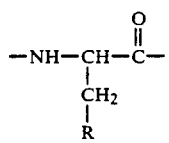

wherein R is (a) a carbocyclic aryl-containing radical selected from the group consisting of naphthyl, anthryl, fluorenyl, phenylanthryl, biphenylyl, benzhydryl and phenyl substituted with three or more straight chain lower alkyl groups; or (b) a saturated carbocyclic radical selected from the group consisting of cyclohexyl substituted with three or more straight chain lower alkyl groups, perhydronaphthyl, perhydrobiphenylyl, perhydro-2,2-diphenylmethyl and adamantyl;

Y is leucyl, isoluecyl, nor-leucyl or N-methyl-leucyl;

Z is glycinamide or —NH—$R_1$, wherein $R_1$ is lower alkyl, cycloalkyl, fluoro lower alkyl or

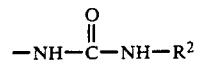

$R_2$ is hydrogen or lower alkyl.

9. A system of claim 8 in which the water-soluble particulate phase comprises about 35 to about 42 weight percent of the matrix.

10. A system of claim 9 in which the water-soluble particulate phase comprises about 39 to about 42 weight percent of the matrix.

11. A system of claim 10 in which the water-soluble particulate phase consists essentially of an LHRH analog or a pharmaceutically acceptable salt thereof.

12. A system of claim 11 in which the LHRH analog is a particulate comprised substantially of agglomerates of primary particles, wherein the primary particles have diameters in the range of less than 0.1 micron to about 1 micron, and the agglomerates have diameters in the range of less than 1 to about 500 microns.

13. The system of claim 11 in which at least 5 percent of the system surface is cut and the remainder is uncut.

14. The system of claim 13 in which at least 50 percent of the system surface is cut.

15. The system of claim 14 in which the LHRH analog is a compound of the formula:

(pyro)Glu-His-V-Ser-W-X-Y-Arg-Pro-Z      (1)

or a pharmaceutically acceptable salt thereof wherein:

V is tryptophyl or phenylalanyl;

W is tyrosyl;

X is 3-(2-naphthyl)-D-alanyl or 3-(2,4,6-trimethylphenyl)-D-alanyl;

Y is leucyl or N-methyl-leucyl; and

Z is glycinamide or —NH—$R^1$, wherein $R_1$ is lower alkyl or

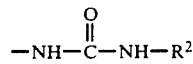

in which $R_2$ is hydrogen or lower alkyl.

16. A system of claim 15 in which the LHRH analog is (pyro)Glu-His-Trp-Ser-Tyr-D-3-(2-naphthyl)alanyl-leu-Arg-Pro-azaglycine amide or a pharmaceutically acceptable salt thereof.

17. A system of claim 16 in which the LHRH analog is the acetate salt, namely (pyro)Glu-His-Trp-Ser-Tyr-D-3-(2-naphthyl)alanyl-leu-Arg-Pro-azaglycine amide acetate.

18. A system of claim 17 in which the LHRH analog is a particulate comprised substantially of agglomerates of primary particles, wherein the primary particles have diameters in the range of less than 0.1 micron to about 1 micron, and the agglomerates have diameters in the range of less than 1 to about 500 microns.

19. A system of claim 17 in which about 60 to 80 percent of the system surface is cut.

20. A system of claim 8 in which the LHRH analog is (pyro)Glu-His-Trp-Ser-Tyr-D-3-(2-naphthyl)alanyl-leu-Arg-Pro-GlyNH$_2$ or a pharmaceutically acceptable salt thereof.

21. The system of claim 20 in which the LHRH analog is the acetate salt, namely (pyro)Glu-His-Trp-Ser-Tyr-D-3-(2-naphthyl)alanyl-leu-Arg-Pro-GlyNH$_2$ acetate.

22. A polymeric delivery system for the controlled and sustained administration of an LHRH analog to an animal in need of such treatment, the system being sized and shaped for placement in the in situ environment of use and consisting essentially of a polydimethylsiloxane elastomer matrix in which is dispersed about 39 to about 42 weight percent of agglomerates of primary particles of (pyro)Glu-His-Trp-Ser-Tyr-D-3-(2-naphthyl)alanyl-leu-Arg-Pro-azaglycide amide acetate, wherein the primary particles have diameters in the range of less than 0.1 micron to about 1 micron, the agglomerates have diameters in the range of less than 1 to about 500 microns, and about 60 to 80 percent of the system surface is cut.

23. A method of continuously administering an LHRH analog at an essentially zero-order therapeutically effective rate to an animal, which method comprises placing an appropriately sized and shaped delivery system in a body site which is capable of making available its intracellular and/or extracellular fluid for transfer into the system, wherein the system comprises a silicone elastomer matrix in which is dispersed about 30 to about 42 weight percent of a water-soluble particulate phase containing an LHRH analog.

24. A method of claim 23 in which the animal is a cat, dog, bovine, pig, horse or human.

25. A method of controlling fertility in animals which comprises placing an appropriately sized and shaped delivery system in a body site which is capable of making available its intracellular and/or extracellular fluid for transfer into the system, wherein the system provides essentially zero-order in vivo delivery of an LHRH analog at an effective rate and comprises a silicone elastomer matrix in which is dispersed about 30 to about 42 weight percent of a water-soluble particulate phase containing an LHRH analog.

26. A method of claim 25 in which the animal is a male dog.

27. A method of claim 25 in which the animal is a female dog.

28. A method of claim 25 in which the animal is a male cat.

29. A method of claim 25 in which the animal is female cat.

30. The method of claim 25 in which the animal is a bovine, pig or horse.

* * * * *